United States Patent
Jeong

(10) Patent No.: US 12,246,151 B2
(45) Date of Patent: Mar. 11, 2025

(54) BILIARY DRAINAGE DEVICE FOR NEGATIVE PRESSURE-RETROGRADE INSTALLATION OF PERCUTANEOUS TRANSHEPATIC BILIARY DRAINAGE

(71) Applicant: Sam Youl Yoon, Seoul (KR)

(72) Inventor: Min Young Jeong, Seoul (KR)

( * ) Notice: Subject to any disclaimer, the term of this patent is extended or adjusted under 35 U.S.C. 154(b) by 0 days.

(21) Appl. No.: 17/630,958

(22) PCT Filed: Jul. 29, 2019

(86) PCT No.: PCT/KR2019/009412
§ 371 (c)(1),
(2) Date: Jan. 28, 2022

(87) PCT Pub. No.: WO2021/020606
PCT Pub. Date: Feb. 4, 2021

(65) Prior Publication Data
US 2022/0265973 A1  Aug. 25, 2022

(51) Int. Cl.
*A61M 27/00* (2006.01)
*A61M 1/00* (2006.01)

(52) U.S. Cl.
CPC .............. *A61M 27/00* (2013.01); *A61M 1/82* (2021.05); *A61M 1/84* (2021.05); *A61M 2210/1071* (2013.01)

(58) Field of Classification Search
CPC .......... A61M 27/00; A61M 1/82; A61M 1/84; A61M 2210/1071; A61M 1/71; A61M 2202/0403; A61M 25/06; A61M 2025/0163; A61M 1/74; A61M 25/00; A61M 27/002; A61M 1/60;
(Continued)

(56) References Cited

U.S. PATENT DOCUMENTS 4,010,756 A * 3/1977 DuMont ............. A61N 1/0587
606/129
6,610,032 B1 * 8/2003 Prody .................. A61M 27/00
604/179
(Continued)

FOREIGN PATENT DOCUMENTS

CN  103284763  9/2013
CN  105413000  3/2016
(Continued)

OTHER PUBLICATIONS

International Search Report and the Written Opinion Dated Apr. 28, 2020 From the International Searching Authority Re. Application No. PCT/KR2019/009412 and Its Translation of Search Report Into English. (10 Pages).
(Continued)

*Primary Examiner* — Philip R Wiest
*Assistant Examiner* — Brandon W. Levy

(57) ABSTRACT

A biliary drainage device for negative pressure-retrograde installation of percutaneous transhepatic biliary drainage (NR-PTBD) according to the present disclosure is in a pancreaticoduodenectomy process, the biliary drainage device including a flexible tube having a suction port formed at one side end and mounted on an afferent loop in order to suck bile; and a guide member installed at the other end of the tube so that the tube inserted through a cut part of a biliary tract can penetrate a liver tissue.

10 Claims, 4 Drawing Sheets

(58) Field of Classification Search
CPC ............ A61M 2039/0279; A61M 1/75; A61M 2210/1082; A61B 2090/037; A61B 17/3415; A61B 17/1114; A61B 10/0283; A61B 17/3478; A61B 17/3401; A61B 17/3403; A61B 17/3421; A61B 2010/045; A61B 2017/3413; A61B 2090/3925; A61B 10/0233; A61B 10/04; A61B 2017/00309; A61B 2017/00867; A61B 1/307; A61B 17/32053; A61B 2017/22044; A61B 17/3417; A61B 1/018; A61B 2017/00323

See application file for complete search history.

(56) References Cited

U.S. PATENT DOCUMENTS

| | | | |
|---|---|---|---|
| 8,267,917 | B2 | 9/2012 | Jabbour et al. |
| 2007/0010798 | A1* | 1/2007 | Stoller .................. A61M 1/81 604/320 |
| 2009/0018507 | A1* | 1/2009 | Schmitz ............. A61B 17/1757 604/164.04 |
| 2012/0123204 | A1* | 5/2012 | Wynberg ............... A61B 1/018 600/106 |
| 2013/0225997 | A1* | 8/2013 | Dillard ............... A61B 10/0233 29/896.9 |
| 2013/0267942 | A1* | 10/2013 | Fulton, III ............. A61B 18/18 606/33 |
| 2016/0022313 | A1* | 1/2016 | Yoshida ............. A61B 17/3478 606/185 |
| 2016/0256615 | A1 | 9/2016 | Poormand |
| 2017/0095234 | A1* | 4/2017 | Prisco ...................... A61B 1/01 |
| 2018/0064918 | A1* | 3/2018 | Aramaki ............. A61M 27/002 |

FOREIGN PATENT DOCUMENTS

| | | |
|---|---|---|
| JP | 06-063046 | 9/1994 |
| KR | 10-2015-0144717 | 12/2015 |
| KR | 20-2017-0002035 | 6/2017 |
| KR | 10-2020-0010838 | 1/2020 |

OTHER PUBLICATIONS

Notification of Office Action and Search Report Dated Nov. 6, 2023 From The State Intellectual Property Office of the People's Republic of China Re. Application No. 201980099048.3 and Its Translation of Office Action Into English. (13 Pages).

* cited by examiner (a)

(b)

(c)

(d)

(a) (b)

(c) (d)

(e) (f)

(a)

(b)

(c)

BILIARY DRAINAGE DEVICE FOR NEGATIVE PRESSURE-RETROGRADE INSTALLATION OF PERCUTANEOUS TRANSHEPATIC BILIARY DRAINAGE

RELATED APPLICATION

This application is a National Phase of PCT Patent Application No. PCT/KR2019/009412 having International filing date of Jul. 29, 2019. The contents of the above application are all incorporated by reference as if fully set forth herein in its entirety.

FIELD AND BACKGROUND OF THE INVENTION

The present disclosure relates to a biliary drainage device for negative pressure-retrogradeinstallation of percutaneous transhepatic biliary drainage, and more particularly, to a biliary drainage device for negative pressure-retrogradeinstallation of percutaneous transhepatic biliary drainage, that is capable of easily and safely performing the negative pressure-retrogradeinstallation of percutaneous transhepatic biliary drainage, in order to reduce the pressure of an afferent loop in a pancreaticoduodenectomy process.

Pancreaticoduodenectomy (pancreatoduodenectomy, Whipple procedure, or Kausch-Whipple procedure) is a basic operation in the surgical treatment of a tumor of the duodenal pylorus. Pancreatic-jejunum anastomosis requires a lot of surgical skill, and the fatality rate due to leakage of such anastomosis is reported to be 25-30%, and the incidence is reported to be about 10-20%. Also, various attempts have been made to prevent the leakage of the pancreatic-jejunum anastomosis by numerous domestic and foreign hepatobiliary and pancreatic surgeons, but there is no definitive answer yet.

Attempts to reduce the leakage of the pancreatic-jejunum anastomosis can be broadly classified into two categories. First is the method of strengthening the anastomosis of an anastomotic part. For example, a study comparing Dunking anastomosis and duct-to-mucosa anastomosis was conducted, and there were cases where pancreaticogastric anastomosis was attempted instead of the pancreatic-jejunum anastomosis, but no meaningful results were obtained. Second is the method of reducing the loading of the afferent loop and lowering the pressure. According to several reports, attempts to reduce the loading of the afferent loop through percutaneous biliary drainage performed before or after surgery have been reported to be meaningful.

Recently, in order to reduce the leakage of pancreatic-jejunum anastomosis part when performing pancreaticoduodenectomy, negative pressure-retrogradeinstallation of percutaneous transhepatic biliary drainage (NR-PTBD) has been developed and attempted by the present inventor. This negative pressure-retrogradeinstallation of percutaneous transhepatic biliary drainage (NR-PTBD) is a method consisting of the following processes. As shown in (a) of FIG. 1, in a state where a biliary tract 2 of a liver 1 is cut during a pancreaticoduodenectomy process, as shown in (b) of FIG. 1, a wire 4 having a blunt end is inserted into an opening of the biliary tract 2 and exposed to a surface of the liver 1, and as shown in (c) of FIG. 1, to the end of the wire 4 that penetrated the liver 1 and is thus exposed, an end of a suction tube 5 is connected, and then as shown in (d) of FIG. 1, by pulling the wire 4, the suction tube 5 connected to the wire 4 is pulled out through the opening of the biliary tract 2. After that, approximately 10-15 cm of the suction tube 5 is mounted on an afferent loop so as to suck pancreatic juice, bile, and intestinal juice, etc., and then, through a drainage bag (Jackson-Pratt drains, not illustrated) connected with the suction tube 5 outside the body, negative pressure is provided to the suction tube 5, to drain the pancreatic juice, bile, and intestinal juice, etc. out of the body, thereby reducing the pressure of the afferent loop.

However, the negative pressure-retrogradeinstallation of percutaneous transhepatic biliary drainage performed during pancreaticoduodenectomy often has a problem where in the process of pulling the wire 4 that has penetrated the liver 1 tissue to induce the suction tube 5, the suction tube 5 may get separated from the wire 4. In such a case where the suction tube 5 is separated from the wire 4 while penetrating the liver tissue, it is necessary to repeat a process of using the wire 4 to make the suction tube 5 penetrate the liver 1 tissue again, connecting the suction tube 5 to the end of the wire 4 again, and then pulling the wire 4 to pull out the suction tube 5 to the opening of the biliary tract 2, and therefore, the liver 1 tissue may be excessively damaged.

Meanwhile, in order to prevent this problem, it is possible to tie the connection part of the wire 4 and the suction tube 5 with a thread so that the fixed state can be firmly maintained, but the connecting operation of the wire 4 and the suction tube 5 has to be performed in an upper part of the liver, that is, in a small space between the liver 1 and the diaphragm 3, which leads to a problem that it extends the operation time and also requires high skill.

SUMMARY OF THE INVENTION

Therefore, a purpose of the present disclosure is to resolve the problems of prior art mentioned above, that is, to provide a biliary drainage device for negative pressure-retrogradeinstallation of percutaneous transhepatic biliary drainage, that is capable of easily and safely performing the negative pressure-retrogradeinstallation of percutaneous transhepatic biliary drainage, in order to reduce the pressure of the afferent loop in a pancreaticoduodenectomy process.

The aforementioned purpose is achieved by a biliary drainage device for negative pressure-retrogradeinstallation of percutaneous transhepatic biliary drainage (NR-PTBD) being performed in a pancreaticoduodenectomy process, the biliary drainage device including a flexible tube having a suction port formed at one side end and mounted on an afferent loop in order to suck bile; and a guide member installed at the other end of the tube so that the tube inserted through a cut part of a biliary tract can penetrate a liver tissue.

Here, it is preferable that the guide member is formed in a rod shape.

Further, it is preferable that multiple guiding grooves are formed on the guide member along a longitudinal direction for bending or cutting of the guide member.

Further, it is preferable that a front end part of the guide member is curved or bent in one direction.

Further, it is preferable that the biliary drainage device further includes a needle being installed after the guide member is removed from the tube so as to penetrate skin after the other end of the tube penetrates the liver tissue.

Further, it is preferable that the needle has a tip part formed at a front end, and a binding part formed at a rear end and being fixed to the tube.

Further, it is preferable that the biliary drainage device further includes a drainage bag being installed after the needle is removed from the tube so as to accommodate the bile being discharged through the tube after the other end of the tube penetrates the skin.

Further, it is preferable that the drainage bag is formed in a bulb shape having elasticity so as to provide negative pressure to the suction port.

According to the present disclosure, there is provided a biliary drainage device for negative pressure-retrogradeinstallation of percutaneous transhepatic biliary drainage, that is capable of easily and safely performing the negative pressure-retrogradeinstallation of percutaneous transhepatic biliary drainage, in order to reduce the pressure of the afferent loop in a pancreaticoduodenectomy process.

Further, since the guide member that penetrates the liver tissue and exits to the outside can be easily bent or cut, there is provided a biliary drainage device for negative pressure-retrogradeinstallation of percutaneous transhepatic biliary drainage, where the guide member that penetrates the liver and is discharged into a small space between the liver and the diaphragm can be easily handled.

Further, there is provided a biliary drainage device for negative pressure-retrogradeinstallation of percutaneous transhepatic biliary drainage, where a front end of the guide member penetrating the liver tissue is bent in one direction, thereby allowing the direction in which the guide member penetrates the liver to be easily controlled.

DESCRIPTION OF SPECIFIC EMBODIMENTS OF THE INVENTION

Figure 1:
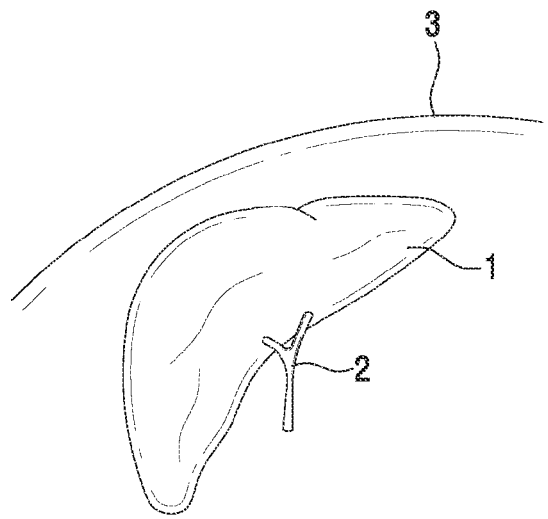
FIG. 1 are schematic views illustrating a conventional negative pressure-retrogradeinstallation of percutaneous transhepatic biliary drainage that may be performed in a pancreaticoduodenectomy process.
Figure 1:
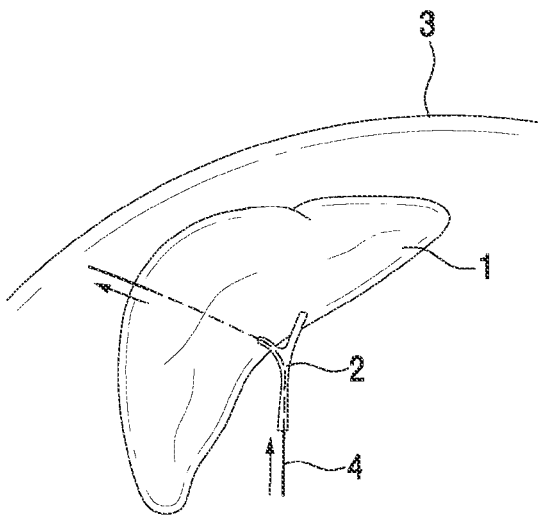
Figure 1:
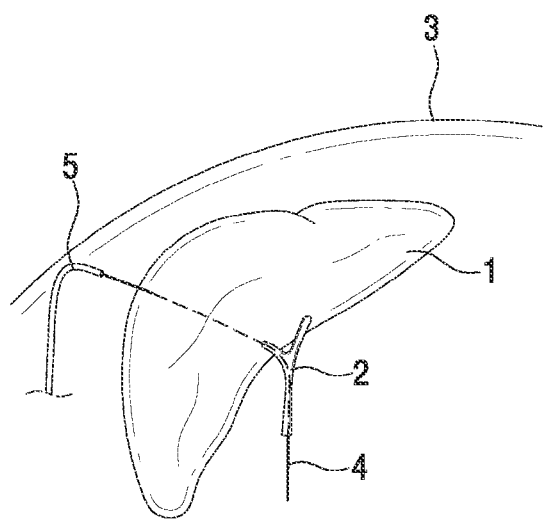
Figure 1:
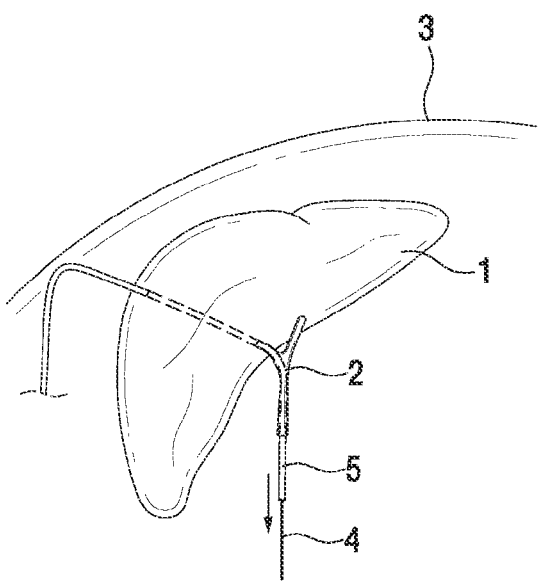
Figure 2:
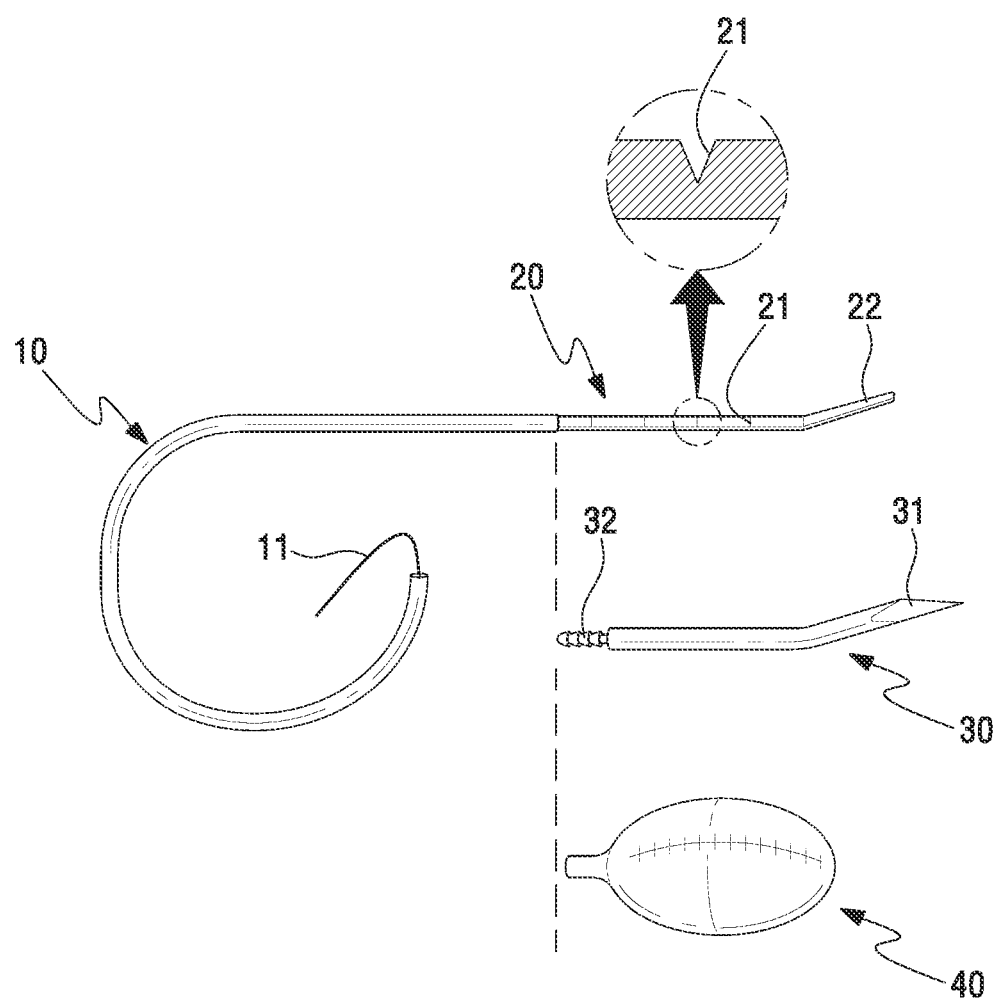
FIG. 2 is a perspective view illustrating a configuration of a biliary drainage device for negative pressure-retrograde-installation of percutaneous transhepatic biliary drainage according to the present disclosure.

For a flexible tube 10 fixed to a rear end of the guide member 20 to be exposed to outside of the liver 1, the entire guide member 20 should come out of the liver 1. Here, as an operator bends or cuts the guide member 20 using the guiding groove 21, it is possible to prevent the guide member 20 from contacting the diaphragm 3 when the entire guide member 20 comes out to a very small space between the liver 1 and the diaphragm 3.

Figure 4:
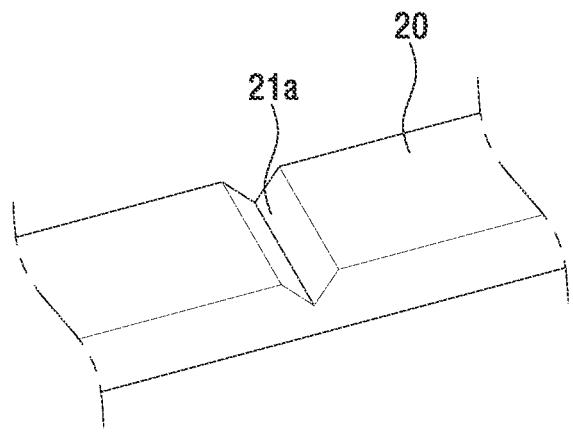
FIG. 4 are views illustrating various embodiments of a guiding groove according to the biliary drainage device for negative pressure-retrogradeinstallation of percutaneous transhepatic biliary drainage according to the present disclosure.
Figure 4:
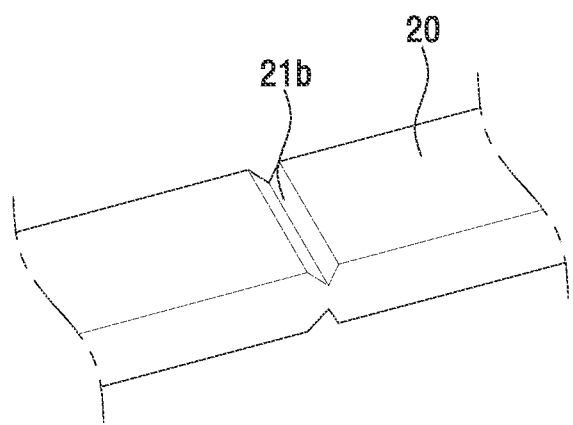
Figure 4:
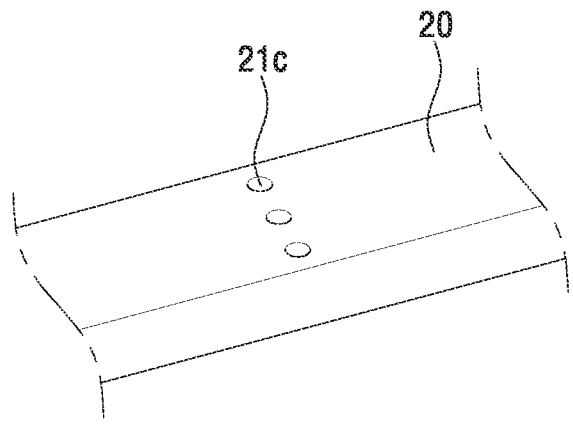

The guiding groove 21 may be configured in various forms depending on the usage environment or purpose. For example, as shown in (a) of FIG. 4, when the guiding groove 21a is recessed from one side of the guide member 20 in a direction transverse to the guide member 20, the guide member 20 can be easily bent in one direction, and as shown in (b) of FIG. 4, when the guiding groove 21b is recessed from both sides of the guide member 20 in the direction transverse to the guide member 20 respectively, the guide member 20 can be cut, or bent to either one selected direction, and as shown in (c) of FIG. 4, when the guiding groove 21c is formed as multiple through holes penetrating the guide member 20, the guide member 20 can be easily cut. It is preferable that such a guiding groove 21 is formed within a range where the guide member 20 is not arbitrarily bent by the guiding groove 21 when the guide member 20 penetrates the liver 1 tissue.

A needle 30 is fixed to the other end of the tube 10 such that the tube 10 can penetrate skin 6 from inside to outside direction. At a front end of the needle 30, a sharp tip part 31 that can penetrate the skin 6, is formed, and at a rear end of the needle 30, a binding part 32 that can be inserted into and fixed to the other end of the tube 10, is formed.

Meanwhile, the tip part 31 may be bent in one direction such that it can penetrate the skin 6 tissue in a small space. Further, the binding part 32 is formed such that it can be inserted into and fixed to the other end of the tube 10, and on an outer circumference surface of the binding part 32, multiple ring-shaped wedges may be provided so as to firmly maintain the fixed state with the tube 10.

The drainage bag 40 is installed after the needle 30 is removed from the tube 10 such that it can accommodate the bile being discharged through the tube 10 after the other end of the tube 10 penetrates the skin 6. In order to provide negative pressure to the suction port 11, the drainage bag 40 may be formed in the shape of a bulb having elasticity.

Hereinbelow, operation of a first embodiment of the aforementioned biliary drainage device for negative pressure-retrogradeinstallation of percutaneous transhepatic biliary drainage will be described.

Figure 3:
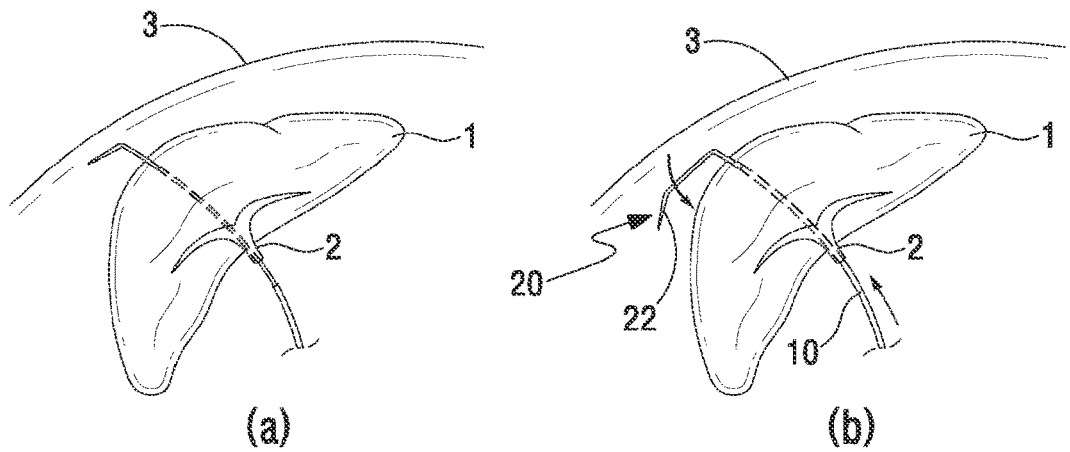
FIG. 3 are schematic views illustrating a negative pressure-retrogradeinstallation of percutaneous transhepatic biliary drainage that may be performed in a pancreaticoduodenectomy process using the biliary drainage device for negative pressure-retrogradeinstallation of percutaneous transhepatic biliary drainage according to the present disclosure.
Figure 3:
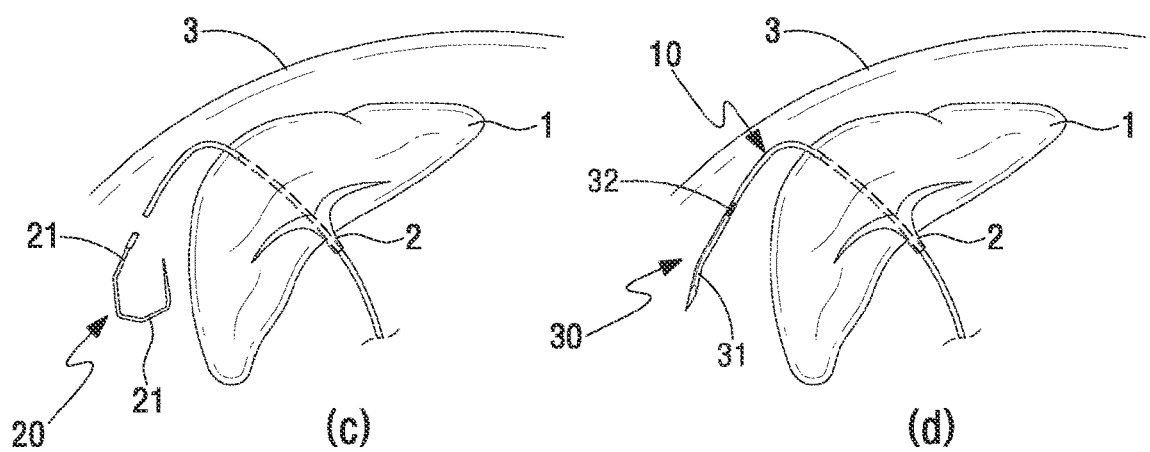
Figure 3:
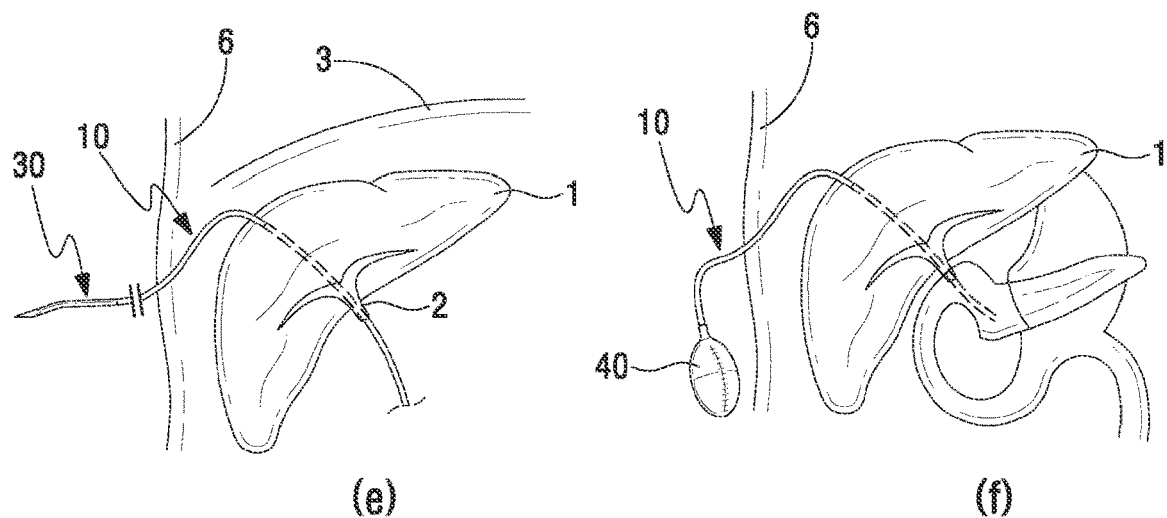

As shown in (a) of FIG. 3, when the front end of the guide member 20 fixed to the end of the tube 10 is inserted into the opening of the biliary tract 2 that has been cut by pancreaticoduodenectomy, and the guide member 20 is pushed in the insertion direction, the front end part 22 of the guide member 20 inserted through the opening of the biliary tract 2 penetrates the liver 1 tissue and thus exposed to outside of the liver 1.

Here, since the front end part 22 of the guide member 20 is bent in one direction, the direction in which the guide member 20 penetrates the liver 1 tissue is guided in the direction in which the front end part 22 is bent. Therefore, the operator can allow the guide member 20 to penetrate the liver 1 tissue in an intended direction while rotating the guide member 20 in axial direction.

Next, as shown in (b) of FIG. 3, in a state where the front end part 22 of the guide member 20 has penetrated the liver 1 tissue and thus exposed to the outside, the front end part 22 of the guide member 20 can be pulled so that the tube 10 connected to the rear end of the guide member 20 penetrates the liver 1 tissue.

According to the present embodiment, the guide member 20 can be bent or cut using the multiple guiding grooves 21 formed along the longitudinal direction of the guide member 20, and thus by bending the guide member 20 exposed to outside of the liver 1 using the guiding groove 21, it is possible to prevent the diaphragm 3 from being damaged by the guide member 20 exposed to outside of the liver 1 inside the small space between the liver 1 and the diaphragm 3. Further, in the present embodiment, the guide member 20 was described as being bent by the guiding groove 21 as an example, but the guide member 20 may be cut instead if necessary.

As shown in (c) of FIG. 3, when the guide member 20 is completely exposed to outside of the liver 1, the tube 10 connected to the rear end of the guide member 20 gets in a state where it has penetrated the liver 1. In such a state, the end of the tube 10 is cut to remove the guide member 20 from the end of the tube 10, and as shown in (d) of FIG. 3, the binding part 32 provided at the rear end of the needle 30 is fixed to the end of the tube 10.

When fixing the needle 30 to the end of the tube 10 is completed, as shown in (e) of FIG. 3, using the tip part 31 of the needle 30, the needle 30 can be operated to penetrate the skin 6, and then the needle 30 can be pulled from outside of the body so that the end of the tube 10 is exposed to outside of the body, and after the end of the tube 10 is exposed to outside of the body, the end of the tube 10 is cut and the needle 30 is removed from the tube 10.

Then, as shown in (f) of FIG. 3, at the end of the tube 10 from which the needle 30 has been removed, a drainage bag 40 is installed, and one side end of the tube 10 extended through the opening of the biliary tract 2 is positioned within the afferent loop that is the pancreatic-jejunum anastomosis part, and then the pancreas, biliary tract 2 and stomach are sutured to the loop respectively through pancreaticoduodenectomy.

After completion of the pancreaticoduodenectomy, when negative pressure is provided through the drainage bag, bile, pancreatic juice, and intestinal juice, etc. can be discharged to outside of the body through the suction port 11 formed at one side end of the tube 10, and thus it is possible to reduce the loading of the afferent loop and lower the pressure, thereby effectively preventing the leakage of pancreatic-jejunum anastomosis.

According to the present embodiment described above, using the guide member 20, the tube 10 inserted into the opening of the biliary tract 2 can be installed in retrograde to the outside of the liver 1, and thus it is possible to easily and safely perform the negative pressure-retrogradeinstallation of percutaneous transhepatic biliary drainage during pancreaticoduodenectomy.

Further, since the guide member 20 penetrating the liver 1 tissue and exiting to the outside can be easily bent or cut, it is possible to prevent the operation becoming difficult due to the guide member 20 exiting in a small space between the liver 1 and the diaphragm 3.

The scope of the present disclose is not limited to the above-described embodiments, but may be implemented in various forms of embodiments within the scope of the appended claims. Without departing from the gist of the present disclosure claimed in the appended claims set, it is considered to be within the scope of the claims of the present disclosure to various extents that can be modified by anyone with ordinary knowledge in the technical field to which the present disclosure pertains.

What is claimed is:

1. A biliary drainage device for negative pressure-retrograde installation of percutaneous transhepatic biliary drainage (NR-PTBD) being performed in a pancreaticoduodenectomy process, the biliary drainage device comprising:
   a flexible tube having a suction port formed at one side end and configured to be mounted on an afferent loop in order to suck bile; and
   a guide member installed at a second end of the tube so that the tube inserted through a cut part of a biliary tract is configured to penetrate a liver tissue;
   wherein the guide member has a portion sized and shaped to be exposed outside of the liver tissue and inside a space between the liver tissue and the diaphragm and has multiple guiding grooves forms along its length that are configured for being cut for a removal of the portion of the guide member.

2. The biliary drainage device for negative pressure-retrograde installation of percutaneous transhepatic biliary drainage (NR-PTBD) being performed in a pancreaticoduodenectomy process, according to claim 1,
   wherein the guide member is formed in a rod shape.

3. The biliary drainage device for negative pressure-retrograde installation of percutaneous transhepatic biliary drainage (NR-PTBD) being performed in a pancreaticoduodenectomy process, according to claim 2,
   wherein a front end part of the guide member is curved or bent in one direction.

4. The biliary drainage device for negative pressure-retrograde installation of percutaneous transhepatic biliary drainage (NR-PTBD) being performed in a pancreaticoduodenectomy process, according to claim 1,
   further comprising a needle being installed after the guide member is removed from the tube so as to penetrate skin after the second end of the tube penetrates the liver tissue.

5. The biliary drainage device for negative pressure-retrograde installation of percutaneous transhepatic biliary drainage (NR-PTBD) being performed in a pancreaticoduodenectomy process, according to claim 4,
   wherein the needle has a tip part formed at a front end, and a binding part formed at a rear end and configured to be fixed to the tube.

6. The biliary drainage device for negative pressure-retrograde installation of percutaneous transhepatic biliary drainage (NR-PTBD) being performed in a pancreaticoduodenectomy process, according to claim 5,
   further comprising a drainage bag being installed after the needle is removed from the tube so as to accommodate the bile being discharged through the tube after the other end of the tube penetrates the skin.

7. The biliary drainage device for negative pressure-retrograde installation of percutaneous transhepatic biliary drainage (NR-PTBD) being performed in a pancreaticoduodenectomy process, according to claim 6,
   wherein the drainage bag is formed in a bulb shape having elasticity so as to provide negative pressure to the suction port.

8. The biliary drainage device for negative pressure-retrograde installation of percutaneous transhepatic biliary drainage (NR-PTBD) being performed in a pancreaticoduodenectomy process, according to claim 1, wherein the multiple guiding grooves comprise a plurality of triangular grooves or multiple holes penetrating the guide member.

9. The biliary drainage device for negative pressure-retrograde installation of percutaneous transhepatic biliary drainage (NR-PTBD) being performed in a pancreaticoduodenectomy process, according to claim 1, wherein the guide member has a rectangular cross section.

10. The biliary drainage device for negative pressure-retrograde installation of percutaneous transhepatic biliary drainage (NR-PTBD) being performed in a pancreaticoduodenectomy process, according to claim 1, wherein the multiple guiding grooves comprise a plurality of grooves at opposite sides of the guide member.

\* \* \* \* \*